United States Patent [19]

Anapliotis

[11] Patent Number: 5,239,981
[45] Date of Patent: Aug. 31, 1993

[54] FILM COVERING TO PROTECT A SURGICAL INSTRUMENT AND AN ENDOSCOPE TO BE USED WITH THE FILM COVERING

[75] Inventor: Emmanuel Anapliotis, Berlin, Fed. Rep. of Germany

[73] Assignee: Effner Biomet GmbH, Berlin, Fed. Rep. of Germany

[21] Appl. No.: 612,848

[22] Filed: Nov. 14, 1990

[30] Foreign Application Priority Data

Nov. 16, 1989 [DE] Fed. Rep. of Germany ... 8913630[U]
Nov. 29, 1989 [DE] Fed. Rep. of Germany ... 8914215[U]

[51] Int. Cl.$^5$ .......................... A61B 1/00; A61M 5/00
[52] U.S. Cl. .......................................... 128/4; 604/171
[58] Field of Search ............ 128/4, 6; 604/171, 172; 433/116; 359/510, 511

[56] References Cited

U.S. PATENT DOCUMENTS

| | | | |
|---|---|---|---|
| 4,033,392 | 7/1977 | Less | 359/511 X |
| 4,266,663 | 5/1981 | Geraci | 359/310 |
| 4,413,278 | 11/1983 | Feinbloom . | |
| 4,522,196 | 6/1985 | Cunningham et al. . | |
| 4,551,137 | 11/1985 | Osborne | 604/171 |
| 4,722,000 | 1/1988 | Chatenever . | |
| 4,723,912 | 2/1988 | Nieusma | 433/116 |
| 4,736,733 | 4/1988 | Adair . | |
| 4,756,304 | 7/1988 | Watanabe . | |
| 4,810,194 | 3/1989 | Snedden | 433/116 X |
| 4,834,068 | 5/1989 | Gottesman . | |
| 4,844,071 | 7/1989 | Chen et al. . | |
| 5,061,246 | 10/1991 | Anapliotis | 604/172 X |

FOREIGN PATENT DOCUMENTS

| | | |
|---|---|---|
| 7802185 | 6/1978 | Fed. Rep. of Germany . |
| 8711189 | 10/1987 | Fed. Rep. of Germany . |
| 3637687 | 5/1988 | Fed. Rep. of Germany . |
| 8812027 | 1/1989 | Fed. Rep. of Germany . |
| 163146 | 5/1921 | United Kingdom . |
| 2148526 | 5/1985 | United Kingdom . |

Primary Examiner—Robert P. Swiatek
Assistant Examiner—Nicholas Lucchesi
Attorney, Agent, or Firm—Spencer, Frank & Schneider

[57] ABSTRACT

A film covering for protecting a surgical instrument such as an endoscope from contamination, includes a tubular film having an inlet opening and an outlet opening disposed opposite to the inlet opening. The outlet opening is formed by an elastic membrane with an aperture, an outer edge of the elastic membrane being stretched and held in a frame which also distends the tubular film.

20 Claims, 2 Drawing Sheets

FILM COVERING TO PROTECT A SURGICAL INSTRUMENT AND AN ENDOSCOPE TO BE USED WITH THE FILM COVERING

CROSS REFERENCE TO RELATED APPLICATION

This application claims the priority of Federal Republic of Germany Application No. G 89 13 630.6 filed Nov. 16, 1989, and the priority of Federal Republic of Germany Application No. 89 14 215.2 filed Nov. 29, 1990 and which are both incorporated herein by reference.

BACKGROUND OF THE INVENTION

This invention relates to a film covering to protect a surgical instrument and to an endoscope to be used with the film covering.

Optical visual aids for medical use are increasingly only designed for screen observation or to be used to document the actual surgical operation sequence. The use of the known ocular observation, i.e. through an eyepiece is mainly restricted to stereoscopic paths of rays and to less time-consuming cases due to the optical and ergonomical disadvantages.

The modern camera endoscopes, which are special instruments to be used with photographic, film or video cameras, are generally of compact construction. In order to protect the valuable cameras and in order to prevent having to sterilize the cameras frequently the cameras and the video and/or other cables are shielded from the surgical wound by film coverings.

Such a film covering is described in DE-GM 88 12 027 and comprises a tubular film open at both ends, whereby the tubular film is folded in a telescopic manner into the inner region of an annular container prior to use. After one end of the tubular film is pulled out of the container the unsterile camera is inserted from one side and the arthroscope through the annular opening of the container from the other side into the tubular film and a sterile connection is made between the arthroscope and the tubular film using tie binders. Then the other end of the tubular film is pulled out of the container and over the part of the tubular film surrounding the camera and is again closed up with a tie binder. The handling of such film coverings is, in particular because of the tie binders, quite time-consuming and requires some skill and is also not reproduceable with respect to the tightness of the connection. The tie binders can in some cases obstruct the handling of the instrument. In addition, a new film covering must be used every time the endoscope or the optical means of the endoscope have to be exchanged during a surgical operation as the connection between the endoscope and the camera is situated inside the film covering.

Another film covering is described in DE-GM 87 11 189 and comprises a tubular film with an inlet and an outlet opening whereby the tubular part is generally folded in a telescopic manner before use. The folding simplifies the insertion of the instrument, for example a camera, which comprises a connection piece and also serves to adapt the length of the film covering to that of the instrument in question. The outlet opening comprises a narrowing of the tube which acts as a stop guide for the instrument to be inserted. When the camera is connected to the arthroscope the tubular film folds in between the contact areas of the connection pieces of the camera and the arthroscope as the diameter of the tubular film is smaller than the diameter of the connection piece of the arthroscope. A disadvantage with this is that the outlet opening formed by the narrowing of the tube has to be quite closely adapted to the cross-section of the part of the instrument to be inserted which means that the number of differently sized film coverings is dependent on the the cross-sections of the instruments used.

SUMMARY OF THE INVENTION

It is an object of the invention to provide a film covering with an improved tightness of the outlet opening and at the same time to simplify the handling and to reduce the number of differently sized film coverings required and to provide an endoscope which leads to fewer film coverings being required and to a less time-consuming replacement procedure.

The above and other objects are accomplished according to the invention by utilizing the realization that in order to connect the sterile part of the instrument to the part of the instrument which is not sterile and which is enveloped by a film covering not only the tie binders, adhesive bands or tie bands but also a narrowing of the tubular film can be replaced by an elastic membrane, which comprises an aperture and whose outer edge stretches and spans a frame which distends the tubular film and thereby improves the tightness of the outlet opening and the handling of the film covering.

The good adaptability of the elastic membrane to the differing cross-sectional shapes and sizes of the parts of the surgical instrument which extend through it is especially advantageous with the film covering according to the invention. If the membrane is of a sufficiently high elasticity one membrane with an aperture of a certain size and therefore one embodiment of the film covering can be used for a plurality of application cases, so that the number of variations required is reduced.

The membrane is preferably circular in shape and comprises a centered aperture which is also circular in shape. Accordingly, the frame comprises contours which are annular or circular and cylindrical in shape as it is connected to the edge of the tubular film and the membrane.

The connection between the frame and the edge of the tubular film comprises a welded connection between an annular, weldable attachment, in particular a soft plastic attachment.

In an advantageous embodiment of the invention the frame comprises a plurality of profiled rings in between which the edge of the tubular film and/or the membrane is fastened. The profiled rings are thereby preferably clamped or screwed together.

The frame is preferably of plastic, whereas rubber, silicon or latex are especially suitable membrane material.

The invention is further based on the realization that by situating a divide in the region of the camera connection piece of a camera endoscope the camera which is enveloped by a film covering can still continue to be used without having to change the film covering if the endoscope or the optical shaft which can be removed from a special endoscope or arthroscope have to be replaced. The divide enables the endoscope to be removed and an essentially cylindrical part of the camera connection part remains attached to the camera. Because the film covering is connected to this camera connection part it can also be avoided that it becomes necessary to reach inside the film covering. In this way the division remains intact even if the optical means have to be replaced—which could occur if the optical means become defective or the viewing width or the direction of view are to be altered.

A further substantial advantage is that during surgery the the outer area remains sterile and the borderline between the sterile and the unsterile areas remains unchanged even when a part which crosses this borderline is replaced. The replacement of the optical means can be carried out quickly and unproblematically so that, for example, during an arthroscopic examination one can at all times quickly adapt the instrument in accordance with the examination conditions. The camera cover, which surrounds the camera and the flexible leads remain fixed to the cylindrical attachment.

It is furthermore particularly advantageous that in this way at least the outer diameter of the partial component of the camera connection piece attached to the camera can be standardized. By standardizing this partial component the number of differently sized film coverings which have to be held in stock can also be reduced as the film covering is connected to this partial component.

The divide between the partial component and the actual endoscope is formed in a uniform manner for all of the exchangeable endoscopes and optical shafts, whereas the connection on the side nearer the camera can either be adapted to correspond with the usual forms of C-mount, bayonet catch or threaded connections or comprises a clamping sleeve which can be pushed over the outer contours of the camera and the partial component. The maximum number of the differing sizes of the partial components corresponds therefore to the number of the camera types used with differing connections or dimensions.

A dovetail connection, a threaded connection ring or a clamped connection, in particular an annular protrusion/annular groove snap-device is situated between the partial component and the remaining exchangeable endoscope in order to enable the endoscope to be replaced quickly. These types of connections which are based on the insertion principle are advantageous because the camera and the endoscope do not have to be rotated with respect to one another during assembly. A correction of the image position or an allround view with inclined optical means is nevertheless possible without any reduction in the sharpness of the picture. A clamping screw is located in the region of the divide in order to fix and in order to be able to find the required rotated position once again. A rotatable optical component can be fixed to the partial component connected to the camera with this clamping screw. The divide can also comprise a bayonet catch or a threaded connection.

In accordance with a further advantageous embodiment of the invention the partial component also carries a projective to project the endoscopic picture onto the recording or film plane of the camera. In this way various subsequent magnifications can be carried out by using a variety of projective optical means. In order to be able to set the sharpness of the picture easily, the partial component preferably comprises a resetting mechanism for the axial displacement of a projective component. This resetting mechanism, in particular a knurled ring, is positioned immediately adjacent to the divide outside the connection area of the film covering.

DESCRIPTION OF THE PREFERRED EMBODIMENT

Figure 1:
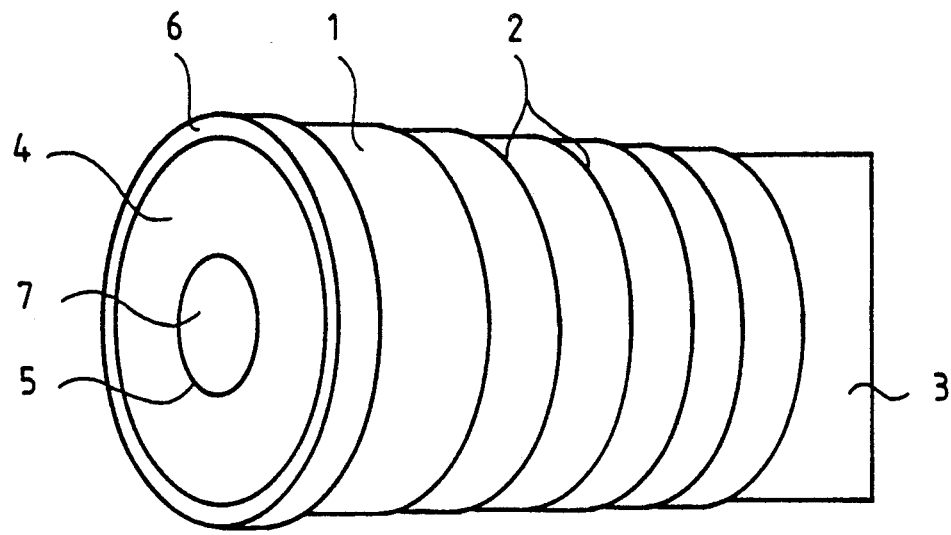
FIG. 1 is a perspective view of the preferred embodiment of the film covering according to the invention.

The film covering illustrated in a perspective view in FIG. 1 comprises a tubular film 1 folded in a telescopic manner 2, an inlet opening 3 and an outlet opening 4. The outlet opening 4 comprises an elastic membrane 5 which is stretched in and spans an annular frame 6. The membrane 5 comprises an aperture 7 for the insertion of the distal end of a surgical instrument, for example a camera, which is to be enveloped. Due to its elasticity the membrane 5 lies in close contact with the outer contours of the instrument part which is to be inserted through the aperture 7 so that a reliable protection against any kind of dirt or contamination can be guaranteed for the enveloped instrument.

Figures 2, 3:
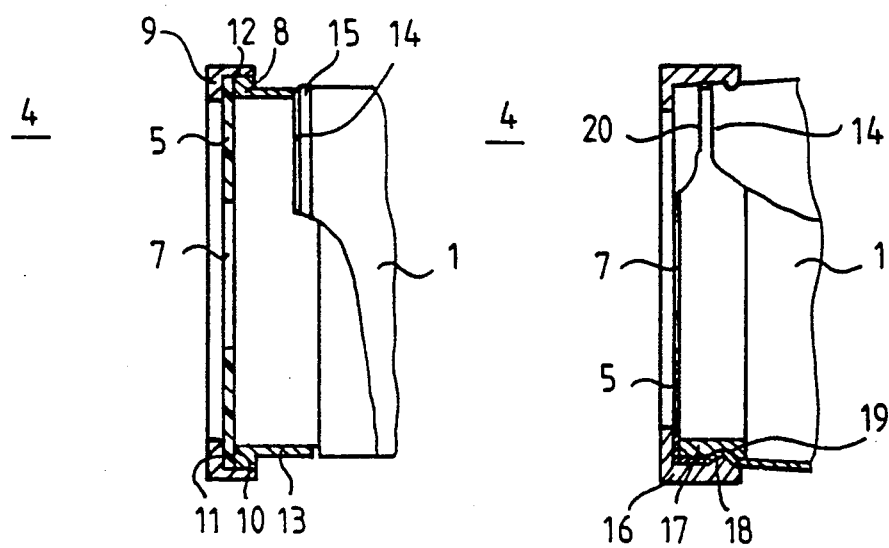
FIG. 2 is a section of a first embodiment of an outlet opening as a detail of the film covering according to FIG. 1.
FIG. 3 is a section of a second embodiment of an outlet opening as a detail of the film covering according to FIG. 1.

FIG. 2 shows a sectional view of a first variation of an outlet opening 4. The frame 6 comprises an inner and an outer threaded ring 8 and 9, whereby the outer threaded ring 9 is shaped as a profiled angle ring. The membrane 5 is clamped firmly between a somewhat wider front face 10 of the inner threaded ring 8 and an inner surface 11 of the profiled angle ring 9. The clamping is achieved by screwing together the rings 8 and 9 which are threaded 12.

The inner threaded ring 8 comprises an annular attachment 13 made of weldable material which is connected to the edge 14 of the tubular film 1 by way of a complete welding seam 15.

A further embodiment of an outlet opening 4 is illustrated in FIG. 3. The frame 6 also consists of two annular parts 16 and 17, but these are not connected together by screwing but by clamping. The outer frame part 16 comprises an annular protrusion 18 on its inner surface which is assigned to an annular groove 19 on the outer surface of the inner frame part 17. The two adjacent areas are both formed in a slightly conical manner. In this way the edge 14 of the tubular film 1 can be pulled over the annular groove 19 of the inner frame part 17 and can be clamped between the protrusion 18 and the groove 19 by pressing the outer frame part 16 without any risk that the edge of the tubular film 14 is pushed back down again from the inner frame part 17 when the outer frame part 16 is pushed onto the inner frame part 17.

Prior to the two frame parts 16 and 17 being connected together the edge of the tubular film 14 is placed over a lower part of the inner frame part 17 and the membrane 5 is placed over the oppositely disposed end surface area of the inner frame part 17. The edge 20 of the annular membrane 5 protrudes minimally out over the end surface area so that the membrane 5 is pulled into the area between the adjacent areas in the direction of the annular groove 19 and is therefore stretched more taughtly when the outer frame part 16 is pressed onto the inner frame part 17.

Figure 4:
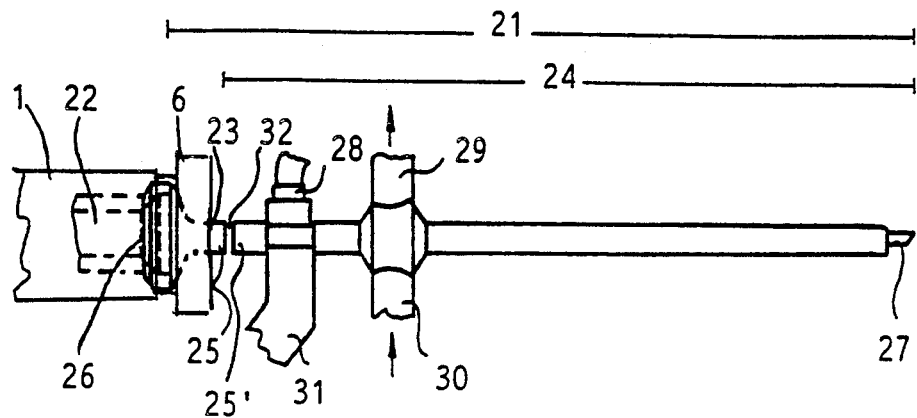
FIG. 4 is a side view of the preferred embodiment of the endoscope in the form of an arthroscope according to the invention with the film covering according to FIG. 1.

In FIG. 4 a camera 22 is protected by being enveloped by a film covering according to the invention and is connected to an arthroscope 21 which comprises a cylindrical partial component 23 on the side nearer the camera and an arthroscopic part 24 which is to be directed towards the joint to be examined arthroscopically. The cylindrical partial component 23 is part of a separable camera connecting piece 25 or 25', which not only serves to mechanically connect the arthroscope 21 to the camera 22 but also serves to optically project the endoscopic interim image onto the reception plane 26 of the camera 21. The remaining arthroscopic part 24 comprises the actual arthroscopic components, namely an optical shaft 27, an optical fiber illumination device 28, a suction device 29, an irrigation device 30, a handle 31 and a part of the camera connection piece 25 or 25'. In order to be able to replace either the arthroscopic part 24, the optical shaft 27 or the camera 22 together with the partial component 23 a divide 32 is situated between the short partial component 23 of the camera connection piece 25 or 25' on the side nearer the camera and the arthroscopic part 24. The partial component 23 comprises a sheath on the side nearer the camera onto which the elastic membrane 5 of the film covering is attached and which also spans and stretches a frame 6. The film covering, together with the frame 6, are pulled over the partial component 23 and the camera 22, whereby the partial component 23, as can be seen in FIG. 5, protrudes out through the aperture 7 of the outlet opening 4 of the film covering.

Figure 5:
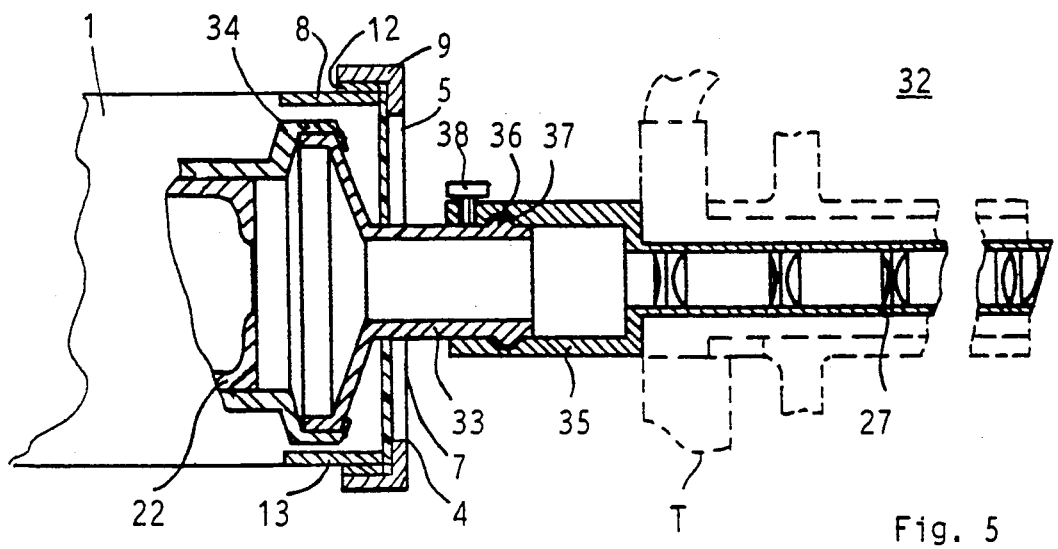
FIG. 5 is a section of the arthroscope according to FIG. 4 with a first embodiment of a divide.

FIG. 5 shows an arthroscope according to FIG. 4 with a more detailed illustration of a first embodiment of the divide 32. The elastic membrane 5 of the outlet opening 4 of the film covering which spans and is stretched by an annular frame 6 comprises an aperture 7 which, due to its elasticity, adapts itself closely to and is connected to the outer contours of the modified partial component 33.

The partial component 33 is connected to the camera 22 via a clamping sleeve 34 at one end and is connected to an essentially hollow-cylindrical attachment connection 35 of the optical shaft 27 at the other end. The divide is formed as a clamped connection and is basically in the form of an annular protrusion/ annular groove snap mechanism. The partial component 33 comprises an annular protrusion 36 on its outer surface and the attachment connection 35 comprises a corresponding annular groove 37 on its inner surface. In order to facilitate the snapping-in of the annular groove 37 into the annular protrusion 36 the attachment connection 35 can be slit in the longitudinal direction. In this way a spring mechanism can be achieved which makes the attachment connection 35 distend further so that it can overcome a more extensive annular protrusion 36 and thereby lead to an improved grip. A clamping screw 38, which can be screwed through the attachment connection 35 adjacent to the annular groove 37 and which can also be screwed tightly against the outer contours of the partial component 33 can be used to fix the rotated positions of the attachment connection 35 and the partial component 33 with respect to each other and thereby can also fix the set rotated positions of the camera 22 and the optical shaft 27 with respect to each other. The inclined view optical shaft 27 is rotatably mounted inside a trepan sheath T—illustrated with dashed lines—which carries the illumination component and the suction/irrigation channels. The optical shaft 27 can also be removed from the trepan sheath. It can be seen that due to this the optical components in the optical shaft 27 can easily be extracted from the trepan sheath for replacement whilst the trepan sheath remains in place after the divide has been opened. This is in particular advantageous during surgical operations as not all of the endoscope needs to be reinserted. It is also not necessary to change the camera and the leads. The replacement of the optical means 27 takes place in the sterile region only. The location of the borderline between the sterile and the unsterile areas of the camera does not change. The clamping screw 38 also allows a detail of the object, which is dependent on the direction of view and therefore dependent on the viewing angle, to be found again more simply as the clamping screw rotates together with the optical means. The replacement of an objective can be carried out quickly whilst requiring only a small number of hand movements which is also of very great importance during surgical operations.

Figure 6:
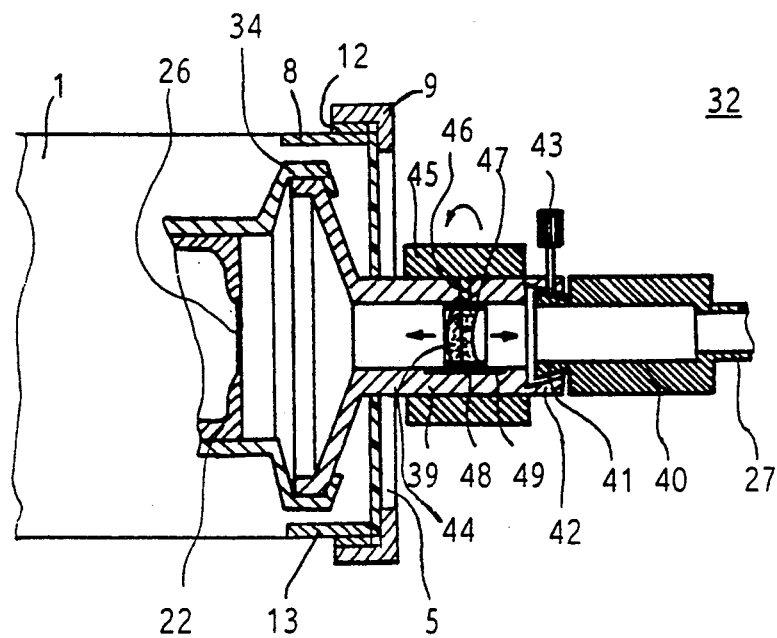
FIG. 6 is a section of a second embodiment of a divide as a detail of the side view according to FIG. 4.

A further embodiment of the divide 32 is illustrated in FIG. 6. The optical shaft 27 is again connected to a corresponding partial component 39 via a rapid replacement device. This rapid replacement device is formed as a dovetail connection whereby an attachment connection 40 of the optical shaft 27 comprises the insert part 41 and the partial component 39 comprises the reception part 42 of the dovetail. The attachment connection 40 and the insert 41 are levered into the dovetail receptor 42 of the partial component 39 and are stopped in the required rotated position by the knurled screw 43.

The partial component 39 is also a carrier of a focusable projective lens system 44. A knurled ring 45, meant for the manual resetting, is rotatably mounted on the partial component 39. A pin 46 which extends through the wall of the partial component 39 is connected to the knurled ring 45 and grips into a guiding groove of a frame 47 which holds the lens system 44 and which runs in a threaded manner. The translatory movement of the lens system 44 is achieved by the forced guidance of the frame 47 by an attachment 48 which is connected to the frame 47 gripping into a longitudinal groove 49 in the inner side of the partial component 39.

It will be understood that the above description of the present invention is susceptible to various modifications, changes and adaptations, and the same are intended to be comprehended within the meaning and range of equivalents of the appended claims.

What is claimed is:

1. A covering for use in protecting a surgical instrument such as an endoscope from contamination, said covering comprising:

a tubular film having at a first end thereof an inlet opening and having a separate outlet means, disposed at a second end opposite to the inlet opening, for receiving a distal end of a surgical instrument;

an annular frame member disposed at the second end of said tubular film for distending the second end of said tubular film;

wherein said outlet means comprises an elastic membrane having an aperture, an outer edge of said elastic membrane being held by said annular frame member, wherein said elastic membrane is stretched in and spans said annular frame member across the second end of said tubular film, and wherein said aperture adapts closely to outer contours of a surgical instrument received by said outlet means due to elasticity of said elastic membrane.

2. The covering as defined in claim 1, wherein said elastic membrane is formed as an annular disc at the second end of said tubular film.

3. The covering as defined in claim 1, wherein said aperture of said elastic membrane comprises a centrally disposed annular aperture.

4. The covering as defined in claim 1, wherein said annular frame membrane comprises means for distending an edge of said tubular film.

5. The covering as defined in claim 4, wherein said annular frame member comprises an annular attachment of weldable material, said annular attachment being welded to said edge of said tubular film.

6. The covering as defined in claim 5, wherein said annular attachment is formed of soft plastic.

7. The covering as defined in claim 4, wherein said annular frame member comprises a plurality of profile rings, between which at least one of said edge of said tubular film and said elastic membrane is held.

8. The covering as defined in claim 7, wherein said profile rings are clamped together.

9. The covering as defined in claim 8, wherein said profile rings comprise an inner and an outer profile ring, the inner comprises an annular groove on an outer surface thereof and the outer profile ring comprises an annular protrusion on an inner surface thereof, whereby positioning of said annular groove and said annular protrusion can be interchanged.

10. The covering as defined in claim 7, wherein said plurality of profile rings are provided with threads by which they screw together.

11. The covering as defined in claim 1, wherein said frame is formed of plastic.

12. The covering as defined in claim 1, wherein said elastic membrane is formed of at least one of the following materials: rubber, silicon or latex.

13. The covering according to claim 1, wherein said tubular film comprises means by which the tubular film can be folded and unfolded in a telescopic manner between said first and second ends thereof.

14. A surgical instrument covering comprising:
a telescoping tubular film having an inlet opening at a first end thereof;
a separate elastic membrane means, disposed and attached to said tubular film at a second end of said tubular film, and having an aperture for receiving a surgical instrument, wherein edges of said aperture come in close contact with outer contours of the surgical instrument when received therein; and
frame means for stretching and holding said elastic membrane means, said elastic membrane means spanning said frame means.

15. The covering according to claim 14, wherein said frame means comprises a plurality of rings between which said elastic membrane means is stretched and held.

16. The covering according to claim 14, wherein said frame means comprises inner and outer interconnecting profile rings, the inner profile ring having an annular groove on an outer surface thereof and the outer profile ring having an annular protrusion on an inner surface thereof.

17. The covering according to claim 14, wherein said elastic membrane means comprises an elastic annular disc.

18. The covering according to claim 14, wherein said aperture of said elastic membrane means comprises a centrally disposed annular aperture.

19. The covering according to claim 14, wherein said frame means comprises an annular attachment of weldable material welded to an edge of said tubular film at the second end thereof.

20. The covering according to claim 14, wherein said frame means comprises inner and outer rings having threads by which they can be screwed together.

* * * * *